United States Patent [19]

Spielvogel et al.

[11] Patent Number: 5,143,907

[45] Date of Patent: Sep. 1, 1992

[54] PHOSPHITE-BORANE COMPOUNDS, AND METHOD OF MAKING AND USING THE SAME

[75] Inventors: Bernard F. Spielvogel, Raleigh; Anup Sood, Durham; Iris H. Hall, Chapel Hill, all of N.C.

[73] Assignee: Boron Biologicals, Inc., Raleigh, N.C.

[21] Appl. No.: 701,682

[22] Filed: May 10, 1991

[51] Int. Cl.$^5$ ............... A61K 31/69; C07F 9/142; C07F 9/141; C07F 9/06
[52] U.S. Cl. ........................... 514/64; 558/72; 562/11
[58] Field of Search ............ 558/72; 562/11; 514/47, 514/48, 49, 51, 64; 536/29

[56] References Cited

U.S. PATENT DOCUMENTS

| | | | |
|---|---|---|---|
| 4,209,510 | 7/1980 | Spielvogel et al. | 424/657 |
| 4,312,989 | 1/1982 | Spielvogel et al. | 546/13 |
| 4,368,194 | 1/1983 | Spielvogel et al. | 514/64 |
| 4,587,359 | 5/1986 | Spielvogel et al. | 564/8 |
| 4,647,555 | 3/1987 | Spielvogel et al. | 514/63 |
| 4,709,083 | 11/1987 | Spielvogel et al. | 560/110 |
| 4,855,493 | 8/1989 | Spielvogel et al. | 562/575 |
| 4,963,655 | 10/1990 | Kinder et al. | 530/331 |

FOREIGN PATENT DOCUMENTS 0034238 4/1985 European Pat. Off.
0336772A2 4/1989 European Pat. Off.

OTHER PUBLICATIONS

Reetz, T., "Trialkyl Borine, A New Type of Phosphorous–Boron Compound", J. Am. Chem. Soc., 1960, 82, 5039–5042.

Primary Examiner—Mary C. Lee
Assistant Examiner—Michael G. Ambrose
Attorney, Agent, or Firm—Steven J. Hultquist

[57] ABSTRACT

Phosphite-borane compounds of the formula $$(R_1O)_3P - \overset{\overset{\displaystyle H}{|}}{\underset{\underset{\displaystyle R_2}{|}}{B}} - R_3$$

wherein:
each $R_1$ is independently selected from: H; $C_1$–$C_{10}$ alkyl; alkylaryl; aralkyl; aryl; monovalent metal ions; nucleosides; and quaternary ammonium ions, $(R_4)_4N^+$, in which the substituents $R_4$ of the ammonium nitrogen atom are H or $C_1$–$C_{10}$ alkyl;
$R_2$ is H or $C_1$–$C_{10}$ alkyl; and
$R_3$ is $CNCH_2CH_3^+BF_4^-$, COOH, carboxyl salts, $COOR_5$, or $CONHR_5$, wherein $R_5$ is $C_1$–$C_{10}$ alkyl, alkylaryl, aralkyl, or aryl;
with the proviso that if at least one of the $R_1$ substituents is H, nucleoside, monovalent metal ion, or quaternary ammonium ion, then $R_3$ may also be CN. The phosphorous-boron adducts of the invention are bioactive in character, variously exhibiting anti-tumor, anti-inflammatory, and hypolipidemic activity. Also disclosed are various synthetic methods for making such phosphorous-boron compounds, and for formulating same in unit dosage forms as well as other pharmaceutically and pharmacologically acceptable formulations.

12 Claims, No Drawings

PHOSPHITE-BORANE COMPOUNDS, AND METHOD OF MAKING AND USING THE SAME

GOVERNMENT RIGHTS IN INVENTION

The invention may be used by the U.S. Government for Governmental purposes without the payment of royalties to the inventors.

BACKGROUND OF THE INVENTION

1. Field of the Invention

The present invention relates to phosphite-borane derivatives that exhibit antineoplastic, anti-hyperlipidemic, and anti-inflammatory activity.

2. Description of the Related Art

Various boron-containing compounds have previously been shown to exhibit therapeutic biological activity. For example, amine-borane compounds such as amine.$BH_2COOH$, amine.$BH_2COOMe$ and amine.$BH_2CONHR$ have been demonstrated to exhibit antitumor, anti-inflammatory and hypolipidemic activities. Additionally, phosphite-borane compounds have been used in hydroboration under mild conditions (Pelter, A., et al, *J. Chem. Soc. Chem. Commun.* (1981), 1014). Since the first reports of phosphite-borane compounds and their properties (Reetz, T., *J. Am. Chem. Soc.* (1960), 82, 5039), very few phosphite-borane compounds have been synthesized and/or had their properties investigated (Das, M. K., et al. *Synth. React. Inorg. Met. Org. Chem.* (1986), 16, 67; Martin, D. R. et al: Pennington, B. T., *J. Inorg. Nucl. Chem.* (1978), 40, 9; and Muttertres, E. L., "The Chemistry of Boron and its Compounds," Wiley, New York, 1967).

Generally, phosphite-borane derivatives may be considered as analogs of alkylphosphates, $(RO)_3P=O$ vs. $(RO)_3PBH_3$, as well as analogs of alkylphosphonates, e.g., $(RO)_2P(O)CH_3$ vs. $(RO)_2P(O)BH_3$, or $(RO)_2P(O)CH_2X$ vs. $(RO)_2P(O)BH_2X$, wherein R is alkyl and X is halo. Since phosphate and phosphonate groups are present in a variety of biologically important molecules, e.g., DNA, RNA, phospholipids, aminophosphonates, etc., their boron-containing analogs may prove useful as biomolecular probes and as potential therapeutic agents.

Additionally, several synthetic phosphonates, e.g., phosphonoacetic acid, phosphonoformic acid, etc., have been found to possess significant antiviral activity (Mayer, R.F., et al, *Antimicrob. Agents Chemother.* (1976), 9, 308; Oberg, B., *Pharmac. Ther.* (1983), 19, 387; and Clerq, E. D., *J. Med. Chem.* (1986), 29, 1561). This antiviral activity coupled with the established pharmacological activity of amine-borane derivatives makes phosphite-borane derivatives potentially significant as a class of bioactive compounds.

While it is clear that considerable potential exists for the utility of phosphite-borane derivatives as biomolecular probes and therapeutic agents, it is equally clear that not much effort has been focused on exploiting this potential. The present invention arose from our ongoing research into boron analogs of biomolecules potentially useful as probes and therapeutic agents.

It therefore is an object of the present invention to provide new phosphite-borane derivatives including active antineoplastic, anti-hyperlipidemic, and anti-inflammatory agents.

It is another object of the present invention to provide new processes for synthesizing phosphite-borane derivatives exhibiting antineoplastic, anti-hyperlipidemic, and anti-inflammatory activity.

Other objects and advantages will be more fully apparent from the ensuing disclosure and appended claims.

SUMMARY OF THE INVENTION

The phosphite-borane derivatives of the present invention include the first phosphite-borane compounds that have been shown to possess significant antitumor, anti-hyperlipidemic, and anti-inflammatory activity. These compounds are significantly different from any phosphite-borane compounds previously known.

The phosphite-borane compounds of the present invention correspond to the general formula:

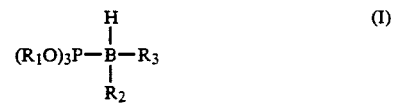

wherein:
each $R_1$ is independently selected from: H; $C_1-C_{10}$ alkyl; alkylaryl; aralkyl; aryl; nucleosides; monovalent metal ions, e.g., Li, Na, K, and the like; and quaternary ammonium cations of the formula $(R_4)_4N^+$, wherein each $R_4$ is independently selected from H and $C_1-C_{10}$ alkyl;

$R_2$ is selected from H and $C_1-C_{10}$ alkyl;

$R_3$ is selected from: $CNCH_2CH_3^+BF_4^-$, COOH, carboxyl salts, $COOR_5$, and $CONHR_5$, wherein $R_5$ is selected from $C_1-C_{10}$ alkyl, alkylaryl, aralkyl, and aryl, with the proviso that if at least one of the $R_1$ substituents is H, nucleoside, monovalent metal ion, or quaternary ammonium cation, then $R_3$ can also be CN.

Another aspect of the present invention relates to processes for preparing phosphite-borane compounds of the above formula. It has been discovered that phosphite-borane derivatives of such type can be prepared (i) from sodium cyanoborohydride by a multi-step process, or (ii) by a one-step process involving a Lewis base exchange reaction. The final products generated by the single-step and multi-step processes, as well as the intermediate products of the multi-step process, comprise phosphite-borane compounds of the present invention.

DETAILED DESCRIPTION OF THE INVENTION

The novel phosphite-borane derivatives of the present invention contain a —P—BHRR'—moiety, as compared to the —P—$BH_2R$—moiety contained in prior art phosphite-borane compounds.

The phosphite-borane derivatives of the present invention correspond to the following general formula:

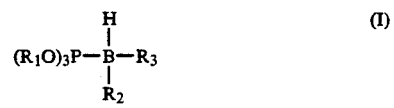

wherein:
each $R_1$ is independently selected from: H; $C_1-C_{10}$ alkyl; alkylaryl; aralkyl; aryl; nucleosides; monovalent metal ions, e.g., Li, Na, K, and the like; and quaternary ammonium cations of the formula $(R_4)_4N^+$, wherein each $R_4$ is independently selected from H and $C_1$-$C_{10}$ alkyl;

$R_2$ is H or $C_1$-$C_{10}$ alkyl;

$R_3$ is selected from $CNCH_2CH_3{}^+BF_4{}^-$, COOH, $COOR_5$, carboxyl salts, and $CONHR_5$, wherein $R_5$ is $C_1$-$C_{10}$ alkyl, alkylaryl, aralkyl, or aryl, with the proviso that if at least one of the $R_1$ substituents is H, nucleoside, monovalent metal ion, e.g., $Li^+$, $Na^+$, $K^+$, etc., or quaternary ammonium ion, $(R_4)_4N^+$, wherein $R_4$ is as described above, then $R_3$ may also be CN.

In the phosphite-borane derivatives of the foregoing formula (I), when $R_1$ is $C_1$-$C_{10}$ alkyl, the alkyl radical may be branched or linear in character. When $R_1$ is alkylaryl or aralkyl, the alkyl moiety of such radicals may likewise be either linear or branched in character. When $R_1$ is a quaternary ammonium cation of the formula $(R_4)_4N^+$, and any of the $R_4$ substituents is $C_1$-$C_{10}$ alkyl, such alkyl substituent preferably is linear in character.

It is to be appreciated that the aliphatic and/or aromatic substituents referred to above may optionally be substituted with heteroatoms or otherwise further substituted, subject to the proviso that such further substitution does not preclude the utility of the resulting compound.

$R_1$ preferably is selected from H, $CH_3$, $CH_2CH_3$, $Na^+$, and $(n-C_4H_9)_4N^+$; $R_2$ preferably is H; and $R_3$ preferably is $CNCH_2CH_3{}^+BF_4{}^-$, COOH, $COOCH_3$, or $CONHCH_2CH_3$.

In a particularly preferred aspect, $R_1$ is $CH_3$ or $CH_2CH_3$; $R_2$ is H; and $R_3$ is COOH, $COOCH_3$, or $CONHCH_2CH_3$.

Exemplary phosphite-borane derivatives of the present invention include the following:

(A) phosphorous acid-cyanoborane, trisodium salt
(B) methylphosphite-cyanoborane
(C) ethylphosphite-cyanoborane
(D) propylphosphite-cyanoborane
(E) dimethylphosphite-cyanoborane
(F) diethylphosphite-cyanoborane
(G) trimethylphosphite-carboxyborane
(H) tripropylphosphite-carboxyborane
(I) diethylphosphite-carboxyborane, sodium salt
(J) diethylphosphite-(N-ethylcarbamoyl) borane
(K) diethylphosphite-(N-ethylcarbamoyl) borane, lithium salt
(L) diethylphosphite-(N-ethylcarbamoyl) borane, tetrabutylammonium salt
(M) triethylphosphite-(N-ethylcarbamoyl) borane
(N) triethylphosphite-carbomethoxyborane
(O) triethylphosphite-carboethoxyborane
(P) triethylphosphite-carbobenzoxyborane
(Q) trimethylphosphite-carbophenoxyborane
(R) diethylphosphite-carbomethoxyborane, potassium salt
(S) diethylphosphite-carbomethoxyborane, ammonium salt
(T) triisopropylphosphite-carbomethoxyborane
(U) tri-n-butylphosphite-carbomethoxyborane
(V) triphenylphosphite-carbomethoxyborane The present invention also comprises methods for preparing the compounds of the present invention. Three distinct processes have been employed to synthesize the compounds of the present invention.

The first, multi-step process which may be used to produce the phosphite-borane derivatives of the present invention utilizes sodium cyanoborohydride as a starting material. This process comprises the following basic steps:

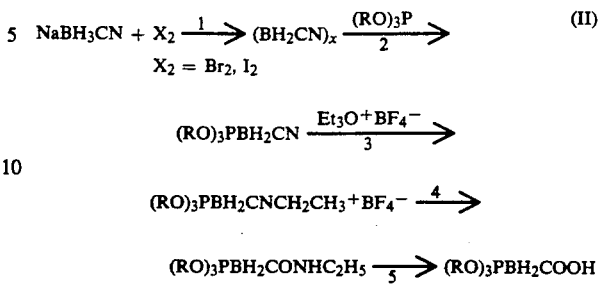

In the above scheme, R is independently selected from: $C_1$-$C_{10}$ alkyl, alkylaryl, aralkyl, or aryl.

The process initially involves: treating $NaBH_3CN$ with $I_2$ or $Br_2$ to form $(BH_2CN)_x$ polymer which then is reacted with $(RO)_3P$ to form phosphite-cyanoborane. The solvent may be any ether, and preferably is tetrahydrofuran (THF). The cyano-substituted product then is alkylated with the alkylating agent $(R_5)_3OBF_4$, wherein $R_5$ is methyl, ethyl, or propyl, and preferably is ethyl. The alkylation may be carried out in a solvent such as dichloromethane or chloroform. The alkylated cyano group then is converted to amide by hydroxide ion in the form of, for example, NaOH, KOH, LiOH, $Mg(OH)_2$, or $Ca(OH)_2$. The amide then is hydrolyzed with dilute acid to form phosphite-carboxyborane.

It should be noted that the above process comprises individual reaction steps which can be individually utilized to prepare a full range of phosphite-borane derivatives of the present invention.

The phosphite-borane derivatives of the present invention can also be prepared by a second process which involves reaction of amine-borane derivatives with a trialkylphosphite to form trialkyl-phosphite-borane derivatives.

A third process which can be used for the preparation of the phosphite-borane derivatives of the invention is the condensation of a mono- or dialkylphosphite-borane derivative with an alcohol, ROH, wherein R is $C_1$-$C_{10}$ alkyl, alkylaryl, aralkyl, aryl, or a nucleoside, e.g., adenosine, guanosine, cytidine, thymidine, or uridine.

The dialkylphosphite-borane derivatives may be prepared from trialkylphosphite-borane derivatives by the following method:

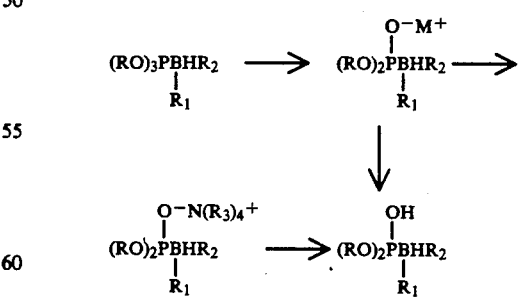

wherein:

R is $C_1$-$C_{10}$ alkyl, alkylaryl, aralkyl, or aryl;

$R_1$ is H or $C_1$-$C_{10}$ alkyl; and $R_2$ is CN, COOH, $CONHR_4$, or $COOR_4$, wherein $R_4$ is $C_1$-$C_{10}$ alkyl, alkylaryl, aralkyl, or aryl; and $R_3$ is H or $C_1$-$C_{10}$ alkyl.

The process involves the reaction of a trialkylphosphite-borane derivative with either (i) OH⁻, e.g., derived from NaOH, KOH, LiOH, Ca(OH)$_2$, etc., or (ii) MI, wherein M is for example Na or K, to produce the metal salt of the dialkylphosphite-borane derivative, which then can be converted to ammonium or other metal salts, or acidified to give the dialkylphosphite-borane derivative.

The monoalkylphosphite-borane derivatives may be prepared by reaction of a di- or trialkylphosphite-borane derivative with trialkylsilyl iodide to form a bis(trialkylsilyl) alkyl phosphite-borane derivative, which then is hydrolyzable to yield a monoalkylphosphite-borane derivative.

The phosphorous acid-borane derivatives may be prepared by reaction of tris(trialkylsilyl)phosphite with an amine-borane derivative followed by basic hydrolysis to give the phosphorous acid-borane derivative salt. The same process may also be used for the mono- and dialkylphosphite-borane derivatives, using (trialkylsilyl)dialkylphosphites or bis(trialkylsilyl) alkylphosphites as the starting materials.

The compounds of the present invention have pharmaceutical activity, including anti-inflammatory, antihyperlipidemic, and antineoplastic activity, and are useful in treating mammals for inflammation, hyperlipidemia, and neoplasia conditions.

A method of combatting hyperlipidemia in an animal subject in need of such treatment comprises administering to the animal subject a hyperlipidemia-combatting amount of a compound of Formula (I).

A method of producing an anti-inflammatory response in an animal subject need of such treatment comprises administering to the animal subject an inflammation-combatting amount of a compound of Formula (I).

A method of combatting tumors, preferably solid tumors (e.g., adenocarcinoma, bronchogenic carcinoma, osteosarcoma, epidermoid carcinoma, breast carcinoma, glioma) in an animal subject in need of such treatment comprises administering to the animal subject a tumor-combatting amount of a compound of Formula (I), after which the tumor preferably is exposed to thermal (low energy neutrons) radiation in an amount effective for $^{10}$B located in the tumor (by virtue of the administration of the compound of Formula (I) to the subject) to capture a neutron, decay, and release an alpha particle in cells of the tumor.

The above-described method of combatting tumors is a preferred modality of anti-tumor treatment; however, in addition to such utility in boron neutron capture therapy, the compounds of Formula (I) also have inherent anti-tumor utility.

Specifically, the compounds of the present invention exhibit cytotoxic activity against colorectal carcinoma, adenocarcinoma, osteosarcoma, breast carcinoma, epidermoid carcinoma, glioma and bronchogenic carcinoma, by functioning as antimetabolites. Correspondingly, the compounds of the present invention facilitate a method of treating a tumor-bearing mammal, comprising administering to such mammal a therapeutically effective amount of a phosphite-borane compound of the present invention.

Subjects to be treated by the methods of the present invention include both human and animal (e.g., bird, dog, cat, cow, horse) subjects, and are preferably mammalian subjects.

Animal subjects are administered compounds of Formula (I) at a daily dose of preferably at least about 0.1 mg/kg weight of the animal subject, more preferably at least about 0.5 mg/kg, and most preferably at least about 2 mg/kg. The daily dose is preferably not more than about 1000 mg/kg, more preferably not more than about 200 mg/kg, and most preferably not more than about 50 mg/kg.

As noted above, the compounds of Formula (I) may be administered per se or in the form of a pharmaceutically acceptable salt. When used in medicine, the salts of the compounds of Formula (I) should be both pharmacologically and pharmaceutically acceptable, but non-pharmaceutically acceptable salts may conveniently be used to prepare the free active compounds or pharmaceutically acceptable salts thereof and are not excluded from the scope of this invention. Where appropriate, such pharmacologically and pharmaceutically acceptable salts include, but are not limited to, those prepared from the following bases: sodium hydroxide, potassium hydroxide, ammonium hydroxide, and calcium hydroxide.

The present invention also provides pharmaceutical formulations, both for veterinary and for human medical use, which comprise the active agent (the compound of Formula (I)) together with one or more pharmaceutically acceptable carriers thereof and optionally any other therapeutic ingredients. The carrier(s) must be pharmaceutically acceptable in the sense of being compatible with the other ingredients of the formulation and not unduly deleterious to the recipient thereof. The active agent is provided in an amount effective to achieve the desired pharmacological effect, as described above, and in a quantity appropriate to achieve the desired daily dose.

The formulations include those suitable for oral, rectal, topical, nasal, ophthalmic, or parenteral (including subcutaneous, intramuscular and intravenous) administration. Formulations suitable for parenteral administration are preferred.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compounds into association with a liquid carrier, a finely divided solid carrier, or both, and then, if necessary, shaping the product into desired formulations.

Formulations of the present invention suitable for oral administration may be presented as discrete units such as capsules, cachets, tablets, or lozenges, each containing a predetermined amount of the active ingredient as a powder or granules; or a suspension in an aqueous liquor or a non-aqueous liquid, such as a syrup, an elixir, an emulsion, or a draught.

A tablet may be made by compression or molding, optionally with one or more accessory ingredients. Compressed tablets may be prepared by compressing in a suitable machine, with the active compound being in a free-flowing form such as a powder or granules which optionally is mixed with a binder, disintegrant, lubricant, inert diluent, surface active agent, or discharging agent. Molded tablets comprised of a mixture of the powdered active compound with a suitable carrier may be made by molding in a suitable machine.

A syrup may be made by adding the active compound to a concentrated aqueous solution of a sugar, for example sucrose, to which may also be added any accessory ingredient(s). Such accessory ingredient(s) may include flavorings, suitable preservatives, agents to retard crystallization of the sugar, and agents to increase the solubility of any other ingredient, such as a polyhydroxy alcohol, for example glycerol or sorbitol.

Formulations suitable for parenteral administration conveniently comprise a sterile aqueous preparation of the active compound, which preferably is isotonic with the blood of the recipient (e.g., physiological saline solution).

Nasal spray formulations comprise purified aqueous solutions of the active compound with preservative agents and isotonic agents. Such formulations are preferably adjusted to a pH and isotonic state compatible with the nasal mucous membranes.

Formulations for rectal administration may be presented as a suppository with a suitable carrier such as cocoa butter, hydrogenated fats, or hydrogenated fatty carboxylic acids.

Ophthalmic formulations are prepared by a similar method to the nasal spray, except that the pH and isotonic factors are preferably adjusted to match that of the eye.

Topical formulations comprise the active compound dissolved or suspended in one or more media, such as mineral oil, petroleum, polyhydroxy alcohols, or other bases used for topical pharmaceutical formulations.

In addition to the aforementioned ingredients, the formulations of this invention may further include one or more accessory ingredient(s) selected from diluents, buffers, flavoring agents, binders, disintegrants, surface active agents, thickeners, lubricants, preservatives (including antioxidants), and the like.

While physiological treatments including veterinary and human treatments, involving administration of phosphite-borane compounds have been described herein with particular reference to the compounds of Formula (I) hereof, it will be appreciated that other phosphite-borane compounds, e.g., those disclosed in Reetz, T., *J. Am. Chem. Soc.*, 1960, 82 5039–5042, may also demonstrate physiological activity and be usefully employed in the broad practice of the present invention.

Further, the phosphite-borane compounds of the invention, as well as other phosphite-borane compounds, may exhibit utility in anti-viral applications involving administration of such compounds to animal (human or veterinary) subjects.

The following Examples are provided to illustrate the present invention, and should not be construed as limiting thereof. Compounds are identified in the first instance by a name and a reference number, and may thereafter be identified solely by reference number, for ease of reference.

In the ensuing Examples, $^1H$ NMR spectra were obtained on JEOL FX90Q, a Brucker NR80, or Varian XL-300 spectrometers. $^{11}B$, $^{13}C$ and $^{31}P$ NMR spectra were obtained on the JEOL FX90Q spectrometer or the Varian XL-300 spectrometer. Chemical shifts are presented with respect to Me$_4$Si for $^1H$ and $^{13}C$ NMR spectra, BF$_3$Et$_2$O for $^{11}B$ NMR spectra and 85% H$_3$PO$_4$ for $^{31}P$ NMR spectra. CDCl$_3$ was used as the solvent unless otherwise stated. IR spectra were obtained on a Perkin-Elmer 297 spectrometer. Elemental analyses were performed by Galbraith Labs, Tennessee, or by M-H-W Labs, Arizona. Analytical and spectroscopic data are presented in Tables I and II set out hereinafter. Due to the quadruple moment of B, the peaks in the boron-11 and phosphorous-31 NMR spectra were broad and the values of $^1J_{B,P}$ obtained from a set of spectra ($^{31}P$ and $^{11}B$) of the same compound were not always identical.

Triethyloxonium tetrafluoroborate, trimethylaminecarboxyborane, trimethylamine-carbomethoxyborane, trimethylamine- and ammonia-N-ethylcarbamoylborane, aniline-, trimethylamine- and triphenylphosphinecyanoborane, and tris(trimethylsilyl)phosphite were prepared by published procedures. All other starting materials were obtained commercially. Anhydrous 1,2-dimethoxyethane (DME) was obtained commercially, while other solvents were dried by routine methods.

As an aid to understanding the ensuing synthesis examples relating to phosphite-borane compounds of the present invention, set out below are synthesis schemes (Scheme 1, Scheme 2, Scheme 3, and Scheme 4) wherein the various compounds of interest are identified numerically, and are hereinafter identified parenthetically by such number.

Scheme 1

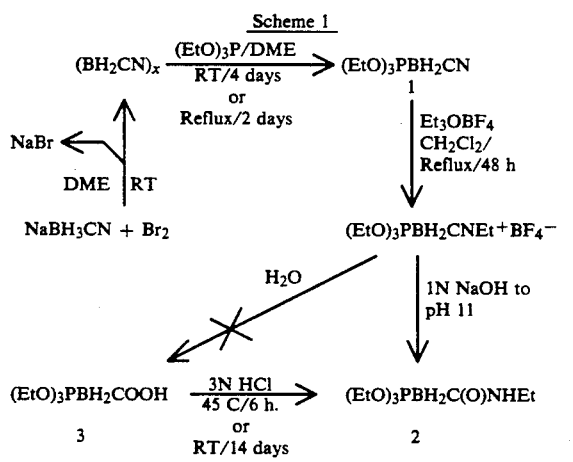

Scheme 2

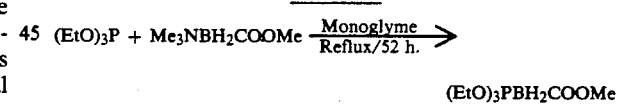

Scheme 3

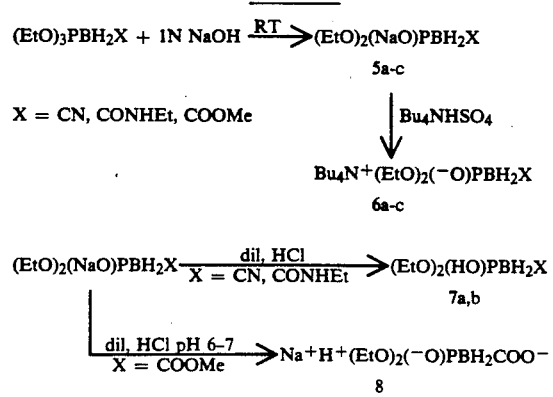

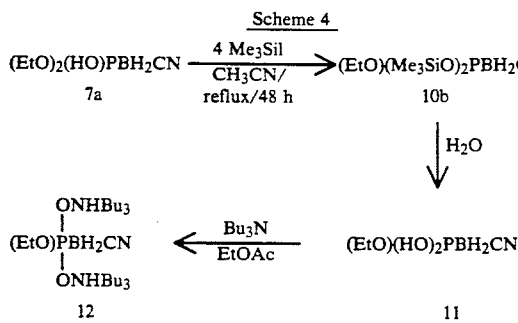

Scheme 4

EXAMPLE I

Synthesis of Triethylphosphite-Cyanoborane (1) From $(BH_2CN)_x$ $NaBH_3CN$ (9.75 g, 155.16 mmol) was dissolved in anhydrous DME (120 ml) under $N_2$. To this a solution of $Br_2$ (3.90 ml, 75.70 mmol) in DME (15 ml) was added dropwise with stirring. The mixture was stirred at room temperature (RT) overnight and then filtered to remove NaBr. The filtrate was mixed with $(EtO)_3P$ (26.10 ml, 152.21 mmol) under $N_2$ and was either stirred at RT for 4 days or heated at reflux for 2 days. It was filtered and the solvent was removed under reduced pressure to give an oil. The oil was dissolved in $Et_2O$ (100 ml), washed with water (5×75 ml), dried over $Na_2SO_4$ and the solvent was removed under reduced pressure. The residue was kept in vacuo for a week to remove traces of triethylphosphate. In most batches, the oil became cloudy, at this point and was rewashed and dried as described above. Attempted distillation under reduced pressure led to decomposition. The pure product (1) can be obtained by keeping it in vacuo for a long time. Yield was 17.91 g, 57.70%.

EXAMPLE II

Synthesis of Triethylphosphite-cyanoborane (1) By Exchange Reaction

Equimolar amounts of $(EtO)_3P$ and an amine-cyanoborane (amine = $PhNH_2$ or $Me_3N$) were taken in anhydrous THF (25 ml) under $N_2$. The mixture was heated at reflux and the reaction was followed by $^{11}B$ NMR. For amine=$PhNH_2$, the reaction was complete in 3.5 hours. After removal of solvent, it was worked up as described in Example I. Yield was 41.32%.

EXAMPLE III

Reaction of Triethylphosphite-cyanoborane (1) With Sodium Iodide

Triethylphosphite-cyanoborane (1) (0.91 g, 4.44 mmol) and NaI (0.665 g, 4.44 mmol) were taken in anhydrous DME under $N_2$ and heated at reflux for 1 hour. The solution was cooled, filtered to remove traces of white solid and the solvent was removed under reduced pressure. The residue was kept in vacuo overnight and analyzed by $^1H$, $^{11}B$ and $^{31}P$ NMR, which showed the reaction product was diethylphosphite-cyanoborane sodium salt (5a).

EXAMPLE IV

Synthesis of Triethylphosphite-N-ethylcarbamoylborane (2) Involving Intermediate Generation of Nitrillium Salt To a stirring solution of triethylphosphite-cyanoborane (1) (9.83 g, 47.95 mmol) in anhydrous $CH_2Cl_2$ (48 ml) under $N_2$, was added a solution of $Et_3OBF_4$ in $CH_2Cl_2$ (48 ml of 2 M solution). The mixture was heated at reflux for 48 hours, cooled to room temperature, and 1 N NaOH was added with stirring until the pH was approximately 11. The layers were separated and the aqueous layer was extracted with $CH_2Cl_2$ (3×75 ml). The combined organic portions were dried and the solvent was removed under reduced pressure to give an oil. The product was purified by flash chromatography on silica using ether:$CH_2Cl_2$ (8:2). Yield was 8.75 g, 72.68%.

EXAMPLE V

Synthesis of Triethylphosphite-Carboxyborane (3)

The conversion of triethylphosphite-N-ethylcarbamoylborane (2) to triethylphosphite-carboxyborane (3) was achieved by hydrolysis with 3N HCl at room temperature or 45° C. At 45° C., the reaction was complete in approximately 6 hours, while at room temperature, two weeks were required for complete hydrolysis. The reaction was also slow at lower concentrations of HCl. Higher concentrations (6N or 12N) of HCl lead to hydrolysis of B-H bonds, to form increasing amounts of boric acid. Boric acid was also the only product, when synthesis of (3) was attempted by an exchange reaction using $(EtO)_3P$ and trimethylamine-carboxyborane or by acid hydrolysis of alkylated cyanoborane. Another route, which was successful, involved the hydrolysis of triethylphosphite-carbomethoxyborane (4). Under similar conditions, the hydrolysis of (4) was much faster than that of (2). The yield of pure product after chromatography, however, was low (ca. 46%).

EXAMPLE VI

Synthesis of Triethylphosphite-Carbomethoxyborane (4)

Triethylphosphite-carbomethoxyborane (4) was prepared in ca. 50% yield, by the reaction of $(EtO)_3P$ with trimethylamine-carbomethoxyborane in refluxing DME, in accordance with Scheme 2, supra. The lower yield was due to loss of product during purification, the exchange itself being greater than 85%. Slower exchange was observed in THF or in a large excess of $(EtO)_3P$ as solvent. In the case where excess $(EtO)_3P$ was used as solvent, an additional species with $^{11}B$ chemical shift similar to (4) was also observed. No attempts were made to isolate this species.

EXAMPLE VII

Synthesis of Diethylphosphite-cyanoborane. Sodium Salt (5a) by Reaction of Triethylphosphite-cyanoborane With Sodium Hydroxide Reaction of triethylphosphite-cyanoborane (1) with 1N NaOH yielded diethylphosphite-cyanoborane, sodium salt (5a). The sodium salt product was isolated by evaporation of water from the reaction product mixture followed by extraction into EtOAc.

EXAMPLE VIII

Synthesis of Diethylphosphite-N-ethylcarbamoylborane, Sodium Salt (5b)

Diethylphosphite-N-ethylcarbamoylborane, sodium salt (5b) was prepared by the same procedure as employed in Example VII, but using triethylphosphite-N-ethylcarbamoylborane as the starting material. Yield was 76.45%.

EXAMPLE IX

Synthesis of Diethylphosphite-carbomethoxyborane, Sodium Salt (5c)

Diethylphosphite-carbomethoxyborane, sodium salt (5c) was prepared by the same procedure as employed in Example VII, but using triethylphosphite-carbomethoxyborane as the starting material. Yield was 91.58%.

EXAMPLE X

Synthesis of Diethylphosphite-cyanoborane, Tetra-n-butylammonium Salt (6a)

1 was hydrolyzed to 5a as described in Example VII. After washing with $CH_2Cl_2$ ($2\times 20$ ml), the basic solution was stirred with $Bu_4NHSO_4$ equivalent.) for 1 hour. It was extracted with dichloromethane ($3\times 35$ ml), dried, and solvent was removed under reduced pressure to give an oil. Yield was 99.01%.

EXAMPLE XI

Synthesis of Diethylphosphite-N-ethylcarbamoylborane. Tetra-n-butylammonium Salt (6b)

Diethylphosphite-N-ethylcarbamoylborane, tetra-n-butylammonium salt (6b) was prepared by the same procedure as employed in Example X, but using diethylphosphite-N-ethylcarbamoylborane as the starting material. The yield of the tetra-n-butylammonium salt product was 91.42%.

EXAMPLE XII

Synthesis of Diethylphosphite-carbomethoxyborane, Tetrabutylammonium Salt (6c)

Diethylphosphite-carbomethoxyborane, tetrabutylammonium salt (6c) was prepared by the same procedure as employed in Example X, but using triethylphosphite-carbomethoxyborane as the starting material. The yield of tetra-n-butylammonium salt product was 97.83%.

EXAMPLE XIII

Synthesis of Diethylphosphite-cyanoborane (7a)

1 (5.75 q, 28.05 mmol) was stirred with 1 N NaOH(180 ml) until dissolution was effected. The solution was washed with $CH_2Cl_2$ ($2\times 50$ ml), acidified with concentrated HCl to pH 1-2, and then extracted with $CH_2Cl_2$. The extracts were dried and the solvent was removed to give a clear, color less oil. The yield of diethylphosphite-cyanoborane was 4.65 g, 93.69%.

EXAMPLE XIV

Synthesis of Diethylphosphite-N-ethylcarbamoylborane (7b)

Diethylphosphite-N-ethylcarbamoylborane (7b) was prepared by the same procedure described in Example XIII, but using triethylphosphite-N-ethylcarbamoylborane (2) as the starting material, and with the solution being acidified to pH 3-4. The yield of diethylphosphite-N-ethylcarbamoylborane was 31.86%.

EXAMPLE XV

Synthesis of Diethylphosphite-carboxyborane, Monosodium Salt (8)

5c was prepared as described in Example IX, then acidified to pH between 6-7. The water in the reaction volume was allowed to evaporate at room temperature. The residue was stirred with EtOAc ($3\times 25$ ml) and filtered. The filtrate was dried and the solvent was removed under reduced pressure to yield a white hygroscopic solvent. Yield of the product was 99.59%.

EXAMPLE XVI

Attempted Synthesis of Diethylphosphite-carboxyborane, Using Triethylphosphite-carboxyborane (3) As a Starting Material Triethylphosphite-carboxyborane (3) (0.15 g, 0.67 mmol) was taken in 1 N NaOH (15 ml) and was heated at 45-47 degrees C. for 7 hours. The mixture was left at room temperature overnight and then washed with $CH_2Cl_2$. The aqueous layer was acidified, extracted with $CH_2Cl_2$, dried, and the solvent was removed to give an oil. Yield was 0.063g.

EXAMPLE XVII

Attempted Synthesis of Diethylphosphite-carboxyborane, Using Diethylphosphite-N-ethylcarbamoylborane (7b) As a Starting Material Diethylphosphite-N-ethylcarbamoylborane (7b) (0.10 g, 0.49 mmol), was taken in 0.3N HCl (10 ml) and the mixture was heated at 42 degrees C. for 6.5 hours. It was extracted with $CH_2Cl_2$ ($4\times 15$ ml). Nothing extracted into the $CH_2Cl_2$. Water was removed from the aqueous layer at room temperature, and the residue was identified by $^{11}B$ NMR. $^{11}B$ nmr: $\delta=20.30$ ppm, s, $H_3BO_3$(major); $-31.55$ ppm, dt; and 31.57 ppm, br.s(minor unknown species).

EXAMPLE XVIII

Attempted Synthesis of Diethylphosphite-carboxyborane, Utilizing Triethylphosphite-carbomethoxyborane (4) As the Starting Material The synthesis of diethylphosphite-carboxyborane was attempted utilizing the procedure of Example XV, but with triethylphosphite-carbomethoxyborane (4) being used as starting material, and with the solution being acidified to lower pH, without success.

EXAMPLE XIX

Attempted Synthesis of Phosphorus Trichloride-cyanoborane

Triphenylphosphine-cyanoborane, $Ph_3PBH_2CN$ (1.00g, 3.32 mmol) and phosphorus trichloride, $PCl_3$ (1 equivalent in tetrahydrofuran, 2 equivalents in trichloromethane, or a large excess as solvent) were taken in an anhydrous solvent under nitrogen atmosphere. The mixture was heated at reflux and the reaction was followed by $^{11}B$ NMR.

EXAMPLE XX

Attempted Synthesis of Phosphorous Acid-Cyanoborane (9) Via Intermediate Formation of Tris(Trimethylsilyl) Phosphite-Cyanoborane (10a)

Aniline-cyanoborane (0.843g, 6.39 mmol) and (Me$_2$SiO)$_3$P (3.82g, 11.79 mmol of (Me$_3$SiO)$_3$P+1.31 mmol of (Me$_3$SiO)$_2$P(O)H) were taken in anhydrous tetrahydrofuran under nitrogen atmosphere. The mixture was heated at reflux for 5 hours and then stirred at room temperature overnight. $^{11}$B NMR$_{CDCl_3}$:$\delta = -38.17$ ppm, dt, $^1J_{B,H}=96 \pm 3$Hz, $^1J_{B,P}=146$ Hz. The solvent was removed under reduced pressure and the residue was kept in vacuo for 5 days. It was taken in ether, filtered, and the solvent was removed under reduced pressure to give a brown oil, which turned purple upon standing. A small portion when taken in D$_2$O, decomposed into boric acid. In 1 N NaOH/D$_2$O, only a small amount of decomposition occurred in the beginning. No further decomposition occurred when it was allowed to stand overnight. The purple oil was dissolved in 1 N NaOH to give phosphorous acid-cyanoborane trisodium salt. The solution was washed with CH$_2$Cl$_2$ (2×50ml) and EtOAc (2×50ml). The aqueous layer was taken with ca. 3 equivalents of Bu$_4$NHSO$_4$, stirred for 30 minutes and then extracted with CH$_2$Cl$_2$ to give an oil (1.064 g). $^{11}$B and $^{31}$P NMR spectra showed no boron or phosphorous.

EXAMPLE XXI

Synthesis of Ethylphosphite-Cyanoborane (11)

Diethylphosphite-cyanoborane (7a) (1.15 g) and Me$_3$SiI (4 equivalents) were taken in anhydrous CH$_3$CN and were heated at reflux in the dark for 2 days. The solvent and excess Me$_3$SiI were removed under reduced pressure. The residue was taken in CH$_2$Cl$_2$/water (1:1, v/v, 50 ml) and was stirred at room temperature for 1.5 hours. The aqueous layer was separated and washed with CH$_2$Cl$_2$ until the organic layer was colorless. The water was evaporated at room temperature by passing a stream of air over the solution. The residue was taken in EtOAc and filtered to remove a solid. The filtrate was dried and the solvent was removed under reduced pressure to give an oil. Often, the EtOAc solution became dark colored, which could not be removed by treatment with charcoal. To remove this color, the EtOAc was removed and the whole work-up was repeated. The yield of light yellow oil was 0.49 g, 50.72%.

EXAMPLE XXII

Synthesis of Ethylphosphite-Cyanoborane, Bis(tributylammonium) Salt (12)

Ethylphosphite-cyanoborane (11) (0.52 g, 3.49 mmol) was taken in EtOAc (5 ml) and was cooled to 0° C. To this Bu$_3$N (2.60 equivalent, excess) was added and the mixture was stirred at 0° C. for 15 minutes. The solution was filtered and the solvent was removed under reduced pressure. The residue was kept in vacuo overnight. The oily residue was washed with n-pentane (3×15 ml), which was removed by decantation. The residue was then taken in CH$_2$Cl$_2$/H$_2$O(1:1, v/v, 30 ml), stirred for 5 minutes and the organic layer was separated. The aqueous layer was extracted with CH$_2$Cl$_2$ (2×15 ml). The combined organic layers were dried and the solvent was removed under reduced pressure to give a clear, colorless oil. The yield of product was 0.85 g, 46.85%.

EXAMPLE XXIII

Attempted Preparation of Tris(trimethylsilyl) Phosphite-Carbomethoxyborane

Me$_3$NBH$_2$COOCH$_3$ (0.80 g, 6.11 mmol) and (Me$_3$SiO)$_3$P (6.06 g, 18.72 mmol of (Me$_3$SiO)$_3$P and 2.08 mmol of (Me$_3$SiO)$_2$P(O)H) were taken in anhydrous DME (40 ml) under nitrogen atmosphere. The mixture was heated at reflux and the reaction was followed by $^{11}$B NMR.

EXAMPLE XXIV

Attempted Preparation of Tris(trimethylsilyl) Phosphite-Carbomethoxyborane

Triethylphosphite-carbomethoxyborane (4) (1.13 g, 4.75 mmol) and Me$_3$SiI 2.70 ml, 18.97 mmol) were taken in anhydrous CH$_3$CN (45 ml) under nitrogen atmosphere. Immediately, the mixture became brown. It was heated at reflux for 3 hours. During this time, the brown color completely disappeared, the mixture was cooled, and the solvent was removed under reduced pressure to give a yellow solid. $^{11}$B NMR $_{CDCl_3}$:$\delta = 15$ ppm, br. s., 0.2 ppm, br. s., major and a multiplet at $-39$ ppm, very small amount.

EXAMPLE XXV

Reaction of Triethylphosphite-Carbomethoxyborane With Iodotrimethylsilane at Room Temperature Triethylphosphite-carbomethoxyborane (4) (0.628 g, 2.64 mmol) and Me$_3$SiI (0.75 ml, 5.27 mmol) were taken in anhydrous CH$_3$CN (30 ml) under nitrogen atmosphere and stirred at room temperature for 6 hours. The mixture was filtered, concentrated, dissolved in CH$_2$Cl$_2$, filtered twice to remove small amounts of white solid (H$_3$BO$_3$) and the solvent was removed under reduced pressure. A small portion was dissolved in acetone-d$^6$ for NMR.

Set out below in Tables 1 and 2 are analytical characterization data for the compounds whose syntheses are variously described in the foregoing Examples I-XXV, including elemental analysis and $^1$H NMR data of the phosphorous-boron adducts (Table 1) and $^{11}$B, $^{31}$P and $^{13}$C NMR and IR data of such phosphorous-boron compounds (Table 2).

TABLE 1

Elemental Analyses and $^1$H NMR Data of Boron Analogs of Phosphonoacetates

| Compound | Formula | Analyses | $^1$H nmr[a] |
|---|---|---|---|
| 1 | BC$_7$H$_{17}$NO$_3$P | C,H,N,P | $\delta$ = 1.39 ppm, t, CH$_3$; 4.20 ppm, m, CH$_2$. |
| 2 | BC$_9$H$_{23}$NO$_4$P | B,C,H,N,P | $\delta$ = 1.09 ppm, t, CH$_3$(NEt); 1.34 ppm, t, CH$_3$; 3.26 ppm, m, CH$_2$(NEt); 4.21 ppm, m, CH$_2$, 5.73 ppm, br.s, NH. |
| 3 | BC$_7$H$_{18}$O$_5$P | C,H; P,B[b] | $\delta$ = 1.34 ppm, t, CH$_3$; 4.17 ppm, m, CH$_2$; 10.11 ppm, br.s, OH. |
| 4 | BC$_8$H$_{20}$O$_5$P | B,C,H,P | $\delta$ = 1.35 ppm, t, CH$_3$, 3.55 ppm, s, OCH$_3$; 4.61 ppm, m, CH$_2$. |
| 5a | BC$_5$H$_{12}$NO$_3$PNa | —[c] | $\delta^d$ = 1.02 ppm, t, CH$_3$; 3.74 ppm, m, CH$_2$. |
| 5b | BC$_7$H$_{18}$NO$_4$PNa | —[c] | $\delta^e$ = 1.11 ppm, t, CH$_3$(NEt); 1.24 ppm, t, CH$_3$; 3.24 ppm, q, NCH$_2$; 3.93 ppm, m, OCH$_2$; NH was not observed. |
| 5c | BC$_6$H$_{15}$O$_5$PNa | —[c] | $\delta^d$ = 1.13 ppm, t, CH$_3$; 3.40 ppm, s, OCH$_3$; 3.83 ppm, m, CH$_2$. |

TABLE 1-continued

Elemental Analyses and $^1$H NMR Data of Boron Analogs of Phosphonoacetates

| Compound | Formula | Analyses | $^1$H nmr$^a$ |
|---|---|---|---|
| 8 | BC$_5$H$_{13}$O$_5$PNa | —$^c$ | $\delta^e$ = 1.35 ppm, t, CH$_3$; 4.02 ppm, m, CH$_2$; no peak was observed for OH, integration of the spectrum however indicated presence of 0.5 H in the region of 10–12 ppm. |
| 6a | BC$_{21}$H$_{48}$N$_2$O$_3$P | B,C,H,N,P | $\delta$ = 1.02 ppm, t, CH$_3$; 1.26 ppm, t, CH$_3$(OEt); 1.46 ppm, m, CH$_2$; 1.67 ppm, br.m, CH$_2$; 3.03 ppm, distorted t, NCH$_2$; 3.95 ppm, m, OCH$_2$. |
| 6b | BC$_{23}$H$_{54}$N$_2$O$_4$P | C,H,N,P; B$^f$ | $\delta$ = 0.80 ppm, t, CH$_3$; 0.86 ppm, t, CH$_3$(NEt); 1.02 ppm, t, CH$_3$; (OEt); 1.24 ppm, m, CH$_2$; 1.45 ppm, br.m, CH$_2$; 2.99 pm, q, CH$_2$(NEt); 3.10 ppm, distorted t, NCH$_2$; 3.72 ppm, m, CH$_2$(OEt); 6.80 ppm, br.t, NH. |
| 6c | BC$_{22}$H$_{51}$NO$_5$P | B,C,H,N,P | $\delta$ = 1.00 ppm, t, CH$_3$, 1.23 ppm, t, CH$_3$(OEt); 1.45 ppm, m, CH$_2$; 1.66 ppm, br.m, CH$_2$; 3.30 ppm, distorted t, NCH$_2$; 3.45 ppm, s, OCH$_3$; 3.94 ppm, m, CH$_2$(OEt). |
| 7a | BC$_5$H$_{13}$NO$_3$P | C,H,N,P | $\delta$ = 1.35 ppm, t, CH$_3$; 4.11 ppm, m, CH$_2$, 9.65 ppm, br.s, OH. |
| 7b | BC$_7$H$_{19}$NO$_4$P | B,C,H,N,P | $\delta$ = 1.15 ppm, t, CH$_3$(NEt); 1.21 ppm, t, CH$_3$; 3.33 ppm, m, CH$_2$(NEt); 3.89 ppm, m, CH$_2$; 8.06 ppm, br.s, NH; 14.50 ppm, br.s, OH. |
| 11 | BC$_3$H$_9$NO$_3$P | —$^c$ | $\delta^e$ = 1.30 ppm, t, CH$_3$; 4.09 ppm, m, CH$_2$; 6.50 ppm, s, OH's, integration >> 2 protons indicating presence of H$_2$O. |
| 12 | BC$_{27}$H$_{63}$N$_3$O$_3$P | $g$ | $\delta$ = 0.92 ppm, br.s, CH$_3$; 1.21 ppm, t, CH$_3$(OEt); 1.35 ppm, br.s, CH$_2$; 1.64 ppm, br.s, CH$_2$; 2.90 ppm, br.s, NCH$_2$; 3.89 ppm, m, OCH$_2$; 11.52 pm, br., NH. |

$^a$All $^3J_{H,H}$ and $^3J_{P,H}$ were close to 7 Hz; BH$_2$ protons were not observed;
$^b$P: calcd, 13.83; found, 13.20; B: calcd, 4.83; found, 4.38;
$^c$Not analyzed, very hygroscopic;
$^d$Solvent used: D$_2$O;
$^e$Solvent used: acetone-d$^6$;
$^f$B: calcd, 2.33, found 1.70;
$^g$Inconsistent with the proposed structure.

TABLE 2

$^{11}$B, $^{31}$P and $^{13}$C NMR and IR Data of Boron Analogs of Phosphonoacetates

| Compound | IR/cm$^{-1}$ | | | | $^{11}$B nmr | | | $^{31}$P nmr |
|---|---|---|---|---|---|---|---|---|
| | $\nu$(BH) | $\nu$(CN) | $\nu$(CO) | Misc. | $\delta$/ppm | $^1J_{B,H}$/Hz | $^1J_{B,P}$/Hz | $\delta$/ppm |
| 1 | 2435, 2400 | 2205 | — | — | −41.57 | 101 ± 1 | 138 ± 1 | 91.90 |
| 2 | 2390 | — | 1600 | $\nu$(NH) 3335 | −31.93 | 95 ± 5 | 117 | 97.90 |
| 3 | 2420 | — | 1655 | $\nu$(OH) 3050, v.br. | −33.76 | 96 ± 1 | 115 | 96.20 |
| 4 | 2415, 2360 | — | 1670 | — | −33.97 | 95 | 122 | 96.59 |
| 5a | 2415, 2370 | 2210 | — | — | −39.62$^b$ | 98 ± 2 | 169 | 68.28$^c$ |
| 5b | | | | | −30.49$^d$ | 88 ± 1 | 149 | 79.97$^d$ |
| 5c | 2430 | — | 1618,1595 | — | −30.79$^b$ | 90 ± 3 | 164 | 73.66$^c$ |
| 8 | 2405 | — | 1645 | $\nu$(OH) v.br. band 3700–2750 | −32.10$^d$ | 95 | 151 | 78.25$^d$ |
| 6a | 2395 | 2195 | — | — | −39.66 | 91 ± 1 | 178 | 69.06 |
| 6b | 2415, 2360, 2320 | — | 1598 | $\nu$(NH) 3340 | −30.49 | 90 | 146 | 77.85 |
| 6c | 2370 | — | 1665 | — | −31.08 | 91 ± 2 | 161 | 73.63 |
| 7a | 2425, 2370 | 2220 | — | — | −40.51 | 103 ± 2 | 141 | 86.06 |
| 7b | 2410 | — | 1615 | $\nu$(NH) 3280 | −33.00 | 91 ± 2 | 163 | 75.19 |
| 11 | 2450 | 2225 | — | — | −39.58$^d$ | 97 ± 1 | 155 ± 1 | 80.56$^d$ |
| 12 | 2390 | 2185 | — | — | −39.32 | $e$ | $e$ | 68.44$^f$ |

| Compound | $^{31}$P nmr $^1J_{B,P}$/Hz | $^{13}$C nmr$^a$ |
|---|---|---|
| 1 | 137 ± 5 | $\delta$ = 15.93 ppm, d, $^3J_{P,C}$ = 5.5 Hz, CH$_3$; 63.96 ppm, d, $^2J_{P,C}$ = 5.5 Hz, CH$_2$. |
| 2 | 118 ± 3 | $\delta$ = 15.03 ppm, s, CH$_3$(NEt); 15.98 ppm, d, $^3J_{P,C}$ = 5.5 Hz, CH$_3$; 32.63 ppm, s, CH$_2$(NEt); 63.03 ppm, d, $^2J_{P,C}$ = 3.3 Hz, CH$_2$. |
| 3 | 119 ± 3 | $\delta$ = 16.01 ppm, d, $^3J_{P,C}$ = 6.6 Hz, CH$_3$; 63.30 ppm, d, $^2J_{P,C}$ = 4.4 Hz, CH$_2$. |
| 4 | 122 | $\delta$ = 16.11 ppm, d, $^3J_{P,C}$ = 6.6 Hz, CH$_3$; 48.67 ppm, s, OCH$_3$; 65.35 ppm, d, $^2J_{P,C}$ = 4.4 Hz, CH$_2$. |
| 5a | 176 ± 3 | $\delta^c$ = 16.65 ppm, d, $^3J_{P,C}$ = 4 Hz, CH$_3$; 57.32 ppm, d, $^2J_{P,C}$ = 5.4 Hz, CH$_2$. |
| 5b | 144 ± 6 | $\delta$ = 15.35 ppm, s, CH$_3$; 16.66 ppm, d, $^3J_{P,C}$ = 5.4 Hz, CH$_3$(OEt); 31.84 ppm, s, NCH$_2$; 57.14 ppm, d, $^2J_{P,C}$ = 5.1 Hz, OCH$_2$. |
| 5c | 160 ± 6 | $\delta^c$ = 16.62 ppm, d, $^3J_{P,C}$ = 5 Hz, CH$_3$; 47.31 ppm, s, OCH$_3$; 57.02 ppm, d, $^2J_{P,C}$ = 5.5 Hz, CH$_2$. |
| 8 | 151 ± 3 | $\delta^d$ = 16.84 ppm, d, $^3J_{P,C}$ = 6.7 Hz, CH$_3$; 59.12 ppm, d, $^2J_{P,C}$ = 5.4 Hz, CH$_2$. |
| 6a | 178 ± 3 | $\delta$ = 13.42 ppm, s, CH$_3$; 16.59 ppm, d, $^3J_{P,C}$ = 5.5 Hz, |

TABLE 2-continued $^{11}$B, $^{31}$P and $^{13}$C NMR and IR Data of Boron Analogs of Phosphonoacetates

| | | |
|---|---|---|
| | | CH$_3$(OEt), 19.47 ppm s, CH$_2$; 23.71 ppm, s, CH$_2$(CH$_2$CH$_2$CH$_3$); 58.03 ppm, s, NCH$_2$; 58.38 ppm, d, $^2$J$_{P,C}$ = 4.4 Hz, CH$_2$(OEt). |
| 6b | 146 ± 3 | δ = 13.33 ppm, s, CH$_3$; 14.98 ppm, s, CH$_3$(NEt); 16.57 ppm, d, $^3$J$_{P,C}$ = 5.5 Hz, CH$_3$(OEt); 19.37 ppm, s, CH$_2$; 23.71 ppm, s, CH$_2$(CH$_2$CH$_2$CH$_3$); 32.05 ppm, s, CH$_2$(NEt); 57.60 ppm, d, $^2$J$_{P,C}$ = 4.4 Hz, CH$_2$(OEt); 58.33 ppm, s, NCH$_2$. |
| 6c | 161 ± 2 | δ = 13.30 ppm, s, CH$_3$; 16.34 ppm, d, $^3$J$_{P,C}$ = 5.4 Hz, CH$_3$(OEt); 19.32 ppm, s, CH$_2$; 23.61 ppm, s, CH$_2$(CH$_2$CH$_2$CH$_3$); 47.50 ppm, s, OCH$_3$; 57.60 ppm, d, $^2$J$_{P,C}$ = 4.0 Hz, CH$_2$(OEt); 58.29 ppm, s, NCH$_2$. |
| 7a | 139 ± 13 | δ = 16.08 ppm, d, $^3$J$_{P,C}$ = 5.5 Hz, CH$_3$; 62.04 ppm, d, $^2$J$_{P,C}$ = 5.5 Hz, CH$_2$. |
| 7b | 161 | δ = 13.77 ppm, s, CH$_3$; 16.30 ppm, d, $^3$J$_{P,C}$ = 6.5 Hz, CH$_3$(OEt); 35.65 ppm, s, CH$_2$; 59.32 ppm, d, $^2$J$_{P,C}$ = 5.5 Hz, CH$_2$(OEt). |
| 11 | 154 ± 5 | δ$^d$ = 16.58 ppm, d, $^3$J$_{P,C}$ = 6.6 Hz, CH$_3$; 61.83 ppm, d, $^2$J$_{P,C}$ = 6.6 Hz, CH$_2$. |
| 12 | 179 ± 5 | δ = 13.46 ppm, s, CH$_3$; 16.51 ppm, d, $^3$J$_{P,C}$ = 6.1 Hz, CH$_3$(OEt); 19.87 ppm, s, CH$_2$; 24.97 ppm, s, CH$_2$(CH$_2$CH$_2$CH$_3$); 51.80 ppm, s, NCH$_2$; 59.10 ppm, d, $^2$J$_{P,C}$ = 5.3 Hz, OCH$_2$. |

$^a$Carbon directly attached to boron was not observed;
$^b$Solvent used: D$_2$O;
$^c$Solvent used: DMSO-d$^6$;
$^d$Solvent used: Acetone-d$^6$;
$^e$Peak was unresolved, therefore the coupling constants couldn't be determined;
$^f$Solvent used: D$_2$O and few drops of Acetone-d$^6$.

EXAMPLE XXVI

Synthesis of 3'-O-acetylthymidine-5'-diethylphosphite-cyanoborane (13)

3'-Acetylthymidine (0.35g, 1.24 mmol), diethylphosphite-cyanoborane (0.22g, 1.24 mmol) and dicyclohexylcarbodiimide, DCC, (2.48 mmol) were taken in anhydrous acetonitrile and the mixture was stirred at room temperature for 48 hours. To the mixture another 2.18 mmol of DCC was added and the mixture was stirred for another 24 hours. After filtration to remove insoluble materials, the solvent was removed under reduced pressure. The residue was taken in dichloromethane (40 ml) and was washed with water (5×30 ml). The organic layer was dried, filtered, and concentrated under reduced pressure. The residue was purified by flash chromatography on silica gel using EtOAc: hexane (9:1). Yield was 0.225g, 46.5%. $^1$H nmr (CDCl$_3$) δ=1.41,t and 1.44,t, 2CH3'$^3$ (OEt); 1.00–1.80, v. br., BH$_2$; 1.98 ppm, s and 1.99 ppm, s, CH$_3$ (for two diastereomers); 2.13 ppm, s, CH$_3$(OAc); 2.30–2.41, m, 2'CH$_2$; 4.15 ppm, m, 4'H; 4.25 ppm, m, CH$_2$'s (OEt); 4.29–4.47 ppm, m, 5'CH$_2$; 5.26 ppm, br., 3'H; 6.43 ppm, m, 1'H; 7.36 ppm, 2 singlets, H6 (for two diastereomers) and 9.20 ppm, s, NH. $^{13}$C nmr (CDCl$_3$): δ=12.35 ppm, s, CH$_3$(C5); 16.02 and 16.10 ppm, 2 doublets, CH$_3$'s (OEt); 20.80 ppm, s, CH$_3$(OAc); 36.54 ppm, s, 2'CH$_2$; 65.19 and 65.33 ppm, 2 doublets, CH$_2$'s (OEt); 65.94 ppm, d, 5'CH$_2$; 74.21 ppm, s, 3'CH; 82.41 ppm, d, 4'CH; 84.06 ppm, s, 1'CH; 112.10 ppm, C5; 134.69 ppm, s, C6; 150.61 ppm, s, C2; 163.61 ppm, s, C4; 170.74 ppm, s, CO(OAc). $^{31}$P nmr (CDCl$_3$): δ=94.26 ppm, br.q., $^1$J$_{B,P}$=156 Hz (based on inner two peaks). FAB MS: MH+: 444.3. Analysis, calculated: % C, 46.07; % H, 6.14; and % N, 9.48. Found: % C, 46.21; % H, 5.94 and % N, 9.37.

EXAMPLE XXVII

Cytotoxic Activity of Phosphorous-Boron Adducts

The synthesized functionalized phosphite-boranes prepared in accordance with the preceding Examples were tested for cytotoxic activity, by preparing a 1 mM solution of the adduct in 0.05% Tween ® 80/H$_2$O solution by homogenization. The resulting drug solutions were sterilized by passage through an Acrodisc 45 μM sterilizer.

The following cell lines were maintained in accordance with literature techniques (literature source indicated parenthetically after identification of the cell line): murine L$_{1210}$ lymphoid leukemia (Geran, R.I., et al. *Cancer Chemotherapy Reports* 1972, 3, 7–9); P$_{388}$ lymphocytic leukemia (Geran, R.I., et al. Ibid); human Tmolt$_3$ acute lymphoblastic T cell leukemia (Minowada, J., et al, *J. Nat. Cancer Int.* 1972, 49, 891–895); colorectal adenocarcinoma SW480 (Liebovitz, A., et al. *Cancer Res.* 1976, 36, 4562–4569); lung bronchogenic MB-9812 (Aaronson, S.A., et al. *Expt. Cell Res.* 1970, 61, 1–5); osteosarcoma TE418 (Smith, H.S., et al. *Int. J. Cancer* 1976, 17, 219–234); KB epidermoid nasal pharynx (Geran, R. I., et al. Ibid.; Eagle, H., *Proc. Soc. Expt. Biol.* 1955, 89, 362–364); HeLa-S$^3$ suspended cervical carcinoma (Puck, T. T., et al. *J. Exp. Med.* 1956, 103, 273–283); and glioma EH 118 Mg (Nelson-Rees, W. A., et al, *Int. J. Cancer* 1975, 16, 74–82).

The protocol used to assess cytotoxicity was that of Geran, et al, *Cancer Chemotherapy Reports,* 1972, 3, 7–9. Standards were determined in each cell line. Values are expressed for the cytotoxicity of the drug as ED$_{50}$ in μg/ml, i.e., the concentration which inhibits 50% of the cell growth determined by the trypan blue exclusion technique. Solid tumor cytotoxicity was determined by the method of Huang, E.S., et al, *J. Pharm. Sci.* 1972, 61, 108–110. Ehrlich ascites carcinoma in vivo tumor screens were conducted in CF$_1$ male mice (~28 g) with test drugs at 8 mg/kg/day I.P. by the method of Geran, et al (supra). 6-Mercaptopurine was used as an internal standard.

The results of the cytotoxicity tests are set out in Table 3 below for compounds 1, 2, 3, 4, 5a, 5b, 5c, 6a, 6b, 6c, 7a, 8, 12, and 13, as well as 5FU, araC, hydroxyurea, cycloleucine, and 6MP.

TABLE 3

Cytotoxicity of Boron Analogues of Phosphonacetates

| Compound # | In Vivo % Inhibition Ehrlich Ascites Carcinoma | ED$_{50}$ ($\mu$g/ml) Cytotoxicity | | | | | | | |
|---|---|---|---|---|---|---|---|---|---|
| | | Murine | | | Human | | | | Osteo |
| | | L$_{1210}$ | P$_{388}$ | Tmolt$_3$ | Colon | HeLa$^3$ | KB | Lung | Glioma | Sarcoma |
| 1 | 66 | 3.61 | | 2.42 | 6.56 | 2.12 | 2.86 | 6.88 | 4.26 | 2.88 |
| 2 | 80 | 4.45 | 6.46 | | | | | | | |
| 3 | 39 | 3.47 | 7.26 | 4.41 | 3.87 | 5.29 | 4.18 | 4.48 | 2.65 | 6.16 |
| 4 | 97 | 4.15 | 4.98 | 3.96 | 1.75 | 1.60 | 7.25 | 4.80 | 6.96 | 7.64 |
| 5a | 70 | 3.15 | 3.62 | | | | | | | |
| 5b | 60 | 2.75 | | 2.89 | 6.40 | 3.50 | 3.67 | 6.80 | 4.53 | 1.52 |
| 5c | 77 | 2.77 | 6.25 | 4.43 | 3.00 | 2.37 | 2.70 | 4.53 | 6.34 | 2.42 |
| 6a | 78 | 3.70 | 7.38 | | | | | | | |
| 6b | 72 | 3.31 | 8.49 | 2.29 | 6.10 | 4.38 | 7.21 | 5.48 | 4.05 | 4.25 |
| 6c | 70 | 2.69 | 5.96 | 2.29 | 3.13 | 1.69 | 5.75 | 3.52 | 5.49 | 3.06 |
| 7a | 94 | 1.62 | 4.11 | 3.36 | 5.56 | 5.25 | 4.01 | 6.39 | 4.01 | 3.91 |
| 8 | 80 | 3.75 | 3.76 | 3.50 | 5.60 | 1.75 | 3.72 | 5.36 | 3.91 | 3.74 |
| 12 | 49 | 3.31 | | 3.56 | 4.24 | 4.83 | 6.67 | 4.89 | 2.87 | 3.53 |
| 13 | 48 | 3.62 | | 4.83 | 2.57 | 2.67 | 3.62 | 4.16 | 5.66 | 5.51 |
| 14 5FU | | 1.41 | 3.72 | 2.14 | 3.09 | 2.47 | 1.25 | 5.64 | 1.28 | |
| araC | | 2.76 | 4.06 | 2.67 | 3.42 | 2.13 | 2.54 | 7.24 | 1.88 | |
| 16 Hydroburea | | 2.67 | | 3.18 | 4.74 | 1.96 | 5.29 | 7.33 | 2.27 | 7.57 |
| 17 Cycloleucine | | 3.08 | | 2.38 | 3.81 | 2.38 | 5.74 | 4.36 | 5.89 | 6.18 |
| 18 6MP | 99 | | | | | | | | | |

Among murine cell lines, most compounds showed activity against L$_{1210}$ lymphoid leukemia growth but only 5a and 8 were active in the P$_{388}$ lymphocytic leukemia screen.

In the human tissue culture lines, most of compounds demonstrated good activity against Tmolt$_3$ leukemia, HeLa-S$^3$ uterine carcinoma and osteosarcoma. In the colon adenocarcinoma screen, only 3, 4, 5c and 6c were significantly active; in the KB nasopharynx carcinoma screen, compounds 1, 5b, 5c and 8 showed good activity. Only 6c demonstrated activity against the lung bronchogenic growth while brain glioma growth was retarded by 3, 8 and 12.

As demonstrated by the data in Table 3, the activity of the functionalized phosphite-boranes in certain screens, e.g., murine L$_{1210}$ and human Tmolt$_3$, is significantly better than that of the standards.

In addition to tissue culture screens, compounds 2, 4, 7a, and 8 were also significantly active against in vivo growth of Ehrlich ascites carcinoma.

EXAMPLE XXVIII

Hypolipidemic Activity of Phosphorous-Boron Adducts

Test compounds (1, 2, 3, 4, 5a, 5b, 5c, 6a, 6b, 6c, 7a, 8, 12, and 13) were suspended in an aqueous 1% carboxymethylcellulose solution, homogenized, and administered to CF$_1$ male mice (~25g) intraperitoneally for 16 days. On days 9 and 16, blood was obtained by tail vein bleeding, and the serum was separated by centrifugation for 3 minutes. Sprague Dawley male rats (~350g) were administered compounds 3, 4, and 8 orally by intubation needle at 20 mg/kg/day. Blood was collected on days 9 and 14. The serum cholesterol levels were determined by a modification of the Liebermann-Burchard reaction (Ness, A.T., et al, *Clin. Chim. Acta.* 1964, 10, 229–237). Serum was also analyzed for triglyceride content by a commercial kit (BioDynamics/bmc) using a BMC single vial triglycerides colorimetric method 348201. Food and water were available ad libitum for animals in the experiments.

In Sprague Dawley rats that had been administered compounds 3, 4, and 8 for 14 days, the liver, small intestine, aorta and fecal materials (24 hour collection) were removed, extracted, and analyzed for cholesterol levels, triglyceride levels (utilizing a BioDynamics/bmc Triglyceride Kit), neutral lipid content, and phospholipid content.

Food consumption was determined in the rat testing as gm food/rat/day for control rats and those treated orally with compound 3, 4, and 8 at 20 mg/kg/day. Body weights were obtained during the experiments and expressed as a percentage of the animal's weight on day 0. After dosing for 14 days with compounds, selected organs were excised, trimmed of fat, and weighed.

In vitro enzymatic studies were determined using 10% homogenates of CF$_1$ male mouse liver with 5–200 $\mu$M concentration of compounds 3 and 4. The enzyme activities were determined by the following literature procedures (Chapman, J.M., Jr., et al, *J. Med. Chem.* 1979, 22, 1399–1402); acetyl coenzyme A synthetase (Hoffmann, G., et al, *Anal. Biochem.* 978, 84, 441–448); adenosine triphosphate dependent citrate lyase (Goodridge, A. G., *J. Biol. Chem.* 1973, 248, 4318–4326); mitochondrial citrate exchange (Robinson, B. H., et al. *Biochim. Biophys. Acta.* 1970, 216, 63–70; and Robinson, B.H., et al. *Eur. J. Biochem.* 1970, 15, 263–272); cholesterol-7$\alpha$-hydroxylase (Shefer, S., et al, *J. Lipid. Res.* 1968, 9, 328–323); 3-hydroxy-3-methylglutaryl coenzyme A reductase (Haven, G.T., et al. *Res. Comm. Chem. Phath. Pharm.* 1973, 6, 253–261; and Wada, F., et al, *J. Biochem.* 1969, 65, 171–175); acetyl coenzyme A carboxylase activity (Greenspan, M. D., et al, *J. Biol. Chem.* 1968, 243, 6373–6280); cholesterol ester hydrolase (Hall, I.H., et al. *Pharm. Res.* 1988, 5, 413–420); sn-glycerol-3-phosphate acyl transferase activity (Lamb, R. G., et al, *Biochim. Biophys. Acta.* 1977, 489, 318–329); phosphatidylate phosphohydrolase activity (Mavis, R. D., et al, *J. Lipid Res.* 1978, 19, 467–477); acyl CoA cholesterol acyl transferase (Balasubramaniam, S., et al, *Eur. J. Biochem.* 1978, 90, 377–383); and heparin activated hepatic lipoprotein lipase (Chait, A., et al. *J. Clin. Invest.* 1982, 69, 490–493). Protein was determined for the cell extract appropriate for each enzyme assay by the Lowry et al technique (Lowry, O. H., et al. *J. Biol. Chem.* 1951, 193, 265–275).

In respect of serum lipoprotein fractions, Sprague Dawley male rats (~300g) were administered compounds 3, 4, and 8 at 20 mg/kg/day orally. Blood was collected from the abdominal aorta vein and lipoprotein fractions were obtained by the method of Hatch and Lees (Hatch, F.T., et al, *Adv. Lipid. Res.* 1968, 1, 1–68) and Havel et al. (Havel, R. J., et al, *J. Clin. Invest.* 1955, 34, 1345–1353), as modified for the rat (in accordance with the procedure of Mookerjea, E.S., et al, *Lipids,* 1975, 10, 374–382). Each of the fractions was analyzed for cholesterol, triglycerides, neutral lipids, phospholipids, and protein levels.

In bile cannulation studies, Sprague Dawley male rats (350g) were administered test drugs 3, 4, and 8 at 20 mg/kg/day orally. On day 14 the rats were anesthetized and the bile duct was cannulated. The bile was collected over the next 6 hours and the flow rate as well as the lipid content determined. The cholic acid content of the bile was determined by the method of Tietz (Tietz, N. W., "Fundamentals of Clinical Chemistry," Saunders, Philadelphia, 1976, pp. 1056–1057).

The results of the foregoing analytical tests are set out below in Table 4 ("The Hypolipidemic Activity of Boron Analogues of Phosphonoacetates in $CF_1$ Mice at 20 mg/kg/day I.P."), Table 5 ("The Effects of Boron Analogues of Phosphonoacetates on Serum Lipids, Tissue Lipids and Serum Lipoproteins After Oral Administration to Sprague Dawley Rats at 20 mg/kg/day"), and Table 6 ("The Effects of Boron Analogues of Phosphonoacetates on Enzyme Activities of Lipid Metabolism of $CF_1$ Mice").

TABLE 4

THE HYPOLIPIDEMIC ACTIVITY OF BORON ANALOGUES OF PHOSPHONOACETATES IN $CF_1$ MICE AT 20 MG/KG/DAY I.P.

| | PERCENT OF CONTROL | | |
|---|---|---|---|
| | SERUM CHOLESTEROL | | SERUM TRIGLYCERIDE |
| [N-6] | DAY 9 | DAY 16 | DAY 16 |
| CONTROL | $100 \pm 6^a$ | $100 \pm 5^b$ | $100 \pm 7^c$ |
| COMPOUND | | | |
| 1 | 81 ± 7* | 68 ± 6* | 72 ± 7* |
| 2 | 71 ± 6* | 64 ± 5* | 54 ± 5* |
| 3 | 67 ± 6* | 59 ± 5* | 50 ± 4* |
| 4 | 67 ± 7* | 54 ± 5* | 46 ± 5* |
| 5a | 83 ± 6 | 78 ± 6* | 54 ± 5* |
| 5b | 69 ± 6* | 72 ± 5* | 81 ± 7 |
| 5c | 61 ± 5* | 56 ± 4* | 81 ± 5* |
| 6a | 83 ± 6 | 68 ± 5* | 39 ± 7* |
| 6b | 74 ± 6* | 56 ± 5* | 68 ± 5* |
| 6c | 76 ± 6* | 77 ± 7* | 60 ± 5* |
| 7a | 85 ± 6 | 87 ± 6 | 71 ± 5* |
| 8 | 74 ± 5* | 51 ± 4* | 53 ± 6* |
| 12 | 59 ± 8* | 58 ± 5* | 78 ± 5* |
| $13^d$ | 77 | 48 | 73 |
| Clofibrate 150 mg/kg/day | 88 ± 7 | 86 ± 6 | 75 ± 5* |

$^a$125 mg %,
$^b$128 mg %,
$^c$137 mg %,
$^d$at 8 mg/kg/day,
*p < 0.001 Student's test

TABLE 5

THE EFFECTS OF BORON ANALOGUES OF PHOSPHONOACETATES ON SERUM LIPIDS, TISSUE AND SERUM LIPOPROTEINS AFTER ORAL ADMINISTRATION TO SPRAGUE DAWLEY RATS AT 20 MG/KG/DAY

| | PERCENT OF CONTROL | | | | | |
|---|---|---|---|---|---|---|
| | SERUM CHOLESTEROL | | SERUM TRIGLYCERIDES | | % BODY WT. | FOOD |
| COMPOUND No. | DAY 7 | DAY 14 | DAY 7 | DAY 14 | DAY 14 | CONSUMP (g/day) |
| CONTROL | $100 \pm 5^a$ | $100 \pm 6^b$ | $100 \pm 7^c$ | $100 \pm 6^d$ | 120 | 20.9 |
| COMPOUND 3 | 70 ± 7* | 73 ± 4* | 76 ± 4* | 69 ± 6* | 153 | 23.57 |
| COMPOUND 4 | 79 ± 5* | 76 ± 6* | 74 ± 7* | 55 ± 3* | 159 | 25.89 |
| COMPOUND 8 | 66 ± 6* | 52 ± 5* | 72 ± 6* | 47 ± 6* | 138 | 25.15 |
| Clofibrate$_e$ | 89 ± 7 | 86 ± 5 | 83 ± 6 | 74 ± 5* | | |
| Lovastatin$_f$ | 85 ± 4 | 82 ± 5* | 91 ± 5 | 86 ± 7 | | |

$^a$75 mg %,
$^b$78 mg %,
$^c$136 mg %.
$^d$139 mg %
$_e$150 mg/kg/day,
$_f$8 mg/kg/day

| BILE LIPIDS | CHOLIC ACID | CHOLESTEROL | TRIGLY-CERIDES | NEUTRAL LIPIDS | POSPHO LIPIDS | PROTEINS |
|---|---|---|---|---|---|---|
| CONTROL | $100 \pm 4^a$ | $100 \pm 5^b$ | $100 \pm 6^c$ | $100 \pm 6^d$ | $100 \pm 5^e$ | $100 \pm 7^f$ |
| COMPOUND 3 | 167 ± 9* | 169 ± 6* | 80 ± 5* | 89 ± 4 | 81 ± 7* | 120 ± 5* |
| COMPOUND 4 | 107 ± 3 | 113 ± 6* | 71 ± 6* | 88 ± 6 | 106 ± 5 | 111 ± 6 |
| COMPOUND 8 | 105 ± 3* | 150 ± 6* | 104 ± 7 | 89 ± 7 | 96 ± 5 | 109 ± 7 |

$^b$118 mg %
$^c$5 mg/ml,
$^d$170 mg/ml,
$^e$1.75 mg/ml,
$^f$3.3 mg %

| LIVER LIPIDS mg/g wet tissue | CHOLIC ACID | CHOLESTEROL | TRIGLY-CERIDES | NEUTRAL LIPIDS | POSPHO LIPIDS | PROTEINS |
|---|---|---|---|---|---|---|
| CONTROL | $100 \pm 6^a$ | $100 \pm 8^b$ | $100 \pm 7^c$ | $100 \pm 6^d$ | $100 \pm 7^e$ | $100 \pm 7^f$ |
| COMPOUND 3 | 87 ± 5* | 102 ± 6 | 78 ± 5* | 105 ± 6 | 98 ± 8 | 97 ± 3* |
| COMPOUND 4 | 86 ± 6 | 88 ± 7 | 83 ± 4* | 119 ± 7 | 47 ± 6 | 75 ± 8 |
| COMPOUND 8 | 71 ± 2* | 95 ± 4 | 83 ± 4 | 141 ± 7* | 47 ± 3* | 89 ± 8 |

$^a$50.5,
$^b$9.18,
$^c$6.37,
$^d$15.76,
$^e$27.19,
$^f$4.5

TABLE 5-continued

THE EFFECTS OF BORON ANALOGUES OF PHOSPHONOACETATES ON SERUM LIPIDS, TISSUE AND SERUM LIPOPROTEINS AFTER ORAL ADMINISTRATION TO SPRAGUE DAWLEY RATS AT 20 MG/KG/DAY

| SMALL INTESTINE mg/g wet tissue | CHOLIC ACID | CHOLESTEROL | TRIGLY-CERIDES | NEUTRAL LIPIDS | POSPHO LIPIDS | PROTEINS |
|---|---|---|---|---|---|---|
| CONTROL | 100 ± 7[a] | 100 ± 6[b] | 100 ± 6[c] | 100 ± 8[d] | 100 ± 5[e] | 100 ± 4[f] |
| COMPOUND 3 | 71 ± 8* | 90 ± 2 | 72 ± 5* | 105 ± 9 | 87 ± 9 | 107 ± 5 |
| COMPOUND 4 | 95 ± 8 | 102 ± 5 | 77 ± 6* | 76 ± 9* | 99 ± 5 | 121 ± 7* |
| COMPOUND 8 | 82 ± 7* | 95 ± 5 | 71 ± 7 | 71 ± 6* | 91 ± 8 | 106 ± 5 |

[a] 62.2,
[b] 12.02
[c] 11.20
[d] 16.98,
[e] 20.06,
[f] 4.2

| AORTA | CHOLIC ACID | CHOLESTEROL | TRIGLY-CERIDES | NEUTRAL LIPIDS | POSPHO LIPIDS | PROTEINS |
|---|---|---|---|---|---|---|
| CONTROL | 100 ± 5[a] | 100 ± 7[b] | 100 ± 8[c] | 100 ± 7[d] | 100 ± 7[e] | 100 ± 5[f] |
| COMPOUND 3 | 91 ± 6 | 54 ± 8* | 134 ± 7* | 102 ± 6 | 91 ± 6 | 87 ± 6 |
| COMPOUND 4 | 62 ± 6* | 32 ± 5* | 115 ± 6 | 80 ± 7 | 125 ± 6* | 72 ± 6* |
| COMPOUND 8 | 101 ± 6 | 70 ± 5* | 132 ± 6* | 97 ± 6 | 106 ± 6 | 85 ± 4 |

[a] 67.5,
[b] 5.77,
[c] 9.86
[d] 15.28,
[e] 28.8,
[f] 11.71

| FECAL | CHOLIC ACID | CHOLESTEROL | TRIGLY-CERIDES | NEUTRAL LIPIDS | POSPHO LIPIDS | PROTEINS |
|---|---|---|---|---|---|---|
| CONTROL | 100 ± 7[a] | 100 ± 5[b] | 100 ± 6[c] | 100 ± 7[d] | 100 ± 8[e] | 100 ± 6[f] |
| COMPOUND 3 | 416 ± 8* | 148 ± 7* | 50 ± 5* | 87 ± 6 | 309 ± 7* | 127 ± 8* |
| COMPOUND 4 | 435 ± 9* | 107 ± 5 | 85 ± 7 | 80 ± 7 | 309 ± 8* | 89 ± 5 |
| COMPOUND 8 | 226 ± 7 | 139 ± 6* | 41 ± 6* | 85 ± 8 | 316 ± 6* | 140 ± 7* |

[a] 11.58,
[b] 2.84
[c] 1.86
[d] 3.39,
[e] 5.70,
[f] 6.99

| SERUM LIPOPROTEIN μg/ml | EXTRACTED LIPIDS | CHOLESTEROL | TRIGLY-CERIDES | NEUTRAL LIPIDS | POSPHO LIPIDS | PROTEINS |
|---|---|---|---|---|---|---|
| CONTROL | | 100 ± 7[a] | 100 ± 7[b] | 100 ± 6[c] | 100 ± 8[d] | 100 ± 6[e] |
| COMPOUND 3 | | 181 ± 6* | 91 ± 6 | 71 ± 6* | 107 ± 5 | 101 ± 8 |
| COMPOUND 4 | | 124 ± 5* | 93 ± 6 | 58 ± 5* | 89 ± 6 | 99 ± 7 |
| COMPOUND 8 | | 127 ± 6* | 90 ± 6 | 68 ± 6 | 43 ± 7* | 100 ± 7 |

[a] 337,
[b] 67,
[c] 420,
[d] 149,
[e] 184.

| VLDL | EXTRACTED LIPIDS | CHOLESTEROL | TRIGLY-CERIDES | NEUTRAL LIPIDS | POSPHO LIPIDS | PROTEINS |
|---|---|---|---|---|---|---|
| CONTROL | | 100 ± 5[a] | 100 ± 6[b] | 100 ± 5[c] | 100 ± 7[d] | 100 ± 5[e] |
| COMPOUND 3 | | 106 ± 3 | 83 ± 3 | 75 ± 5* | 58 ± 8* | 171 ± 6* |
| COMPOUND 4 | | 187 ± 6* | 121 ± 6* | 95 ± 7 | 89 ± 6 | 167 ± 6* |
| COMPOUND 8 | | 47 ± 7* | 84 ± 6 | 94 ± 7 | 113 ± 6 | 154 ± 7* |

[a] 190,
[b] 98,
[c] 221,
[d] 26,
[e] 50.

| LDL | EXTRACTED LIPIDS | CHOLESTEROL | TRIGLY-CERIDES | NEUTRAL LIPIDS | POSPHO LIPIDS | PROTEINS |
|---|---|---|---|---|---|---|
| CONTROL | | 100 ± 7[a] | 100 ± 6[b] | 100 ± 5[c] | 100 ± 7[d] | 100 ± 6[e] |
| COMPOUND 3 | | 69 ± 8* | 102 ± 4 | 133 ± 7 | 39 ± 7* | 80 ± 5* |
| COMPOUND 4 | | 80 ± 5* | 78 ± 5* | 150 ± 6* | 137 ± 5* | 78 ± 6* |
| COMPOUND 8 | | 122 ± 5* | 64 ± 5* | 170 ± 5* | 153 ± 6* | 83 ± 3* |

[a] 210,
[b] 10,
[c] 45,
[d] 41,
[e] 122.

| HDL | EXTRACTED LIPIDS | CHOLESTEROL | TRIGLY-CERIDES | NEUTRAL LIPIDS | POSPHO LIPIDS | PROTEINS |
|---|---|---|---|---|---|---|
| CONTROL | | 100 ± 6[a] | 100 ± 5[b] | 100 ± 9[c] | 100 ± 6[d] | 100 ± 4[e] |
| COMPOUND 3 | | 107 ± 5 | 218 ± 5* | 87 ± 5 | 457 ± 7* | 81 ± 6 |
| COMPOUND 4 | | 204 ± 7* | 98 ± 6 | 158 ± 6* | 533 ± 7* | 139 ± 7* |

TABLE 5-continued
THE EFFECTS OF BORON ANALOGUES OF PHOSPHONOACETATES ON SERUM LIPIDS, TISSUE AND SERUM LIPOPROTEINS AFTER ORAL ADMINISTRATION TO SPRAGUE DAWLEY RATS AT 20 MG/KG/DAY

| COMPOUND 8 | 275 ± 8* | 88 ± 5 | 70 ± 8* | 86 ± 7* | 121 ± 7* |
|---|---|---|---|---|---|

[a]540,
[b]27,
[c]620,
[d]153,
[e]637.

TABLE 6
THE EFFECTS OF BORON ANALOGUES OF PHOSPHONOACETATES ON ENZYME ACTIVITIES OF LIPID METABOLISM OF $CF_1$ MICE

| | CONTROL | | COMPOUND 3 | | | COMPOUND 4 | |
|---|---|---|---|---|---|---|---|
| ENZYME ASSAY | | 25 μM | 50 μM | 100 μM | 25 μM | 50 μM | 100 μM |
| MITOCHONDRIAL CITRATE EXCHANGE[a] | 100 ± 6 | 82 ± 3 | 72 ± 4* | 120 ± 6 | 174 ± 6* | 365 ± 6* | 459 ± 4* |
| ATP-DEPENDENT CITRATE LYASE[b] | 100 ± 6 | 45 ± 4* | 35 ± 4* | 30 ± 3* | 46 ± 6* | 25 ± 5* | 25 ± 4* |
| ACETYL CoA SYNTHETASE[c] | 100 ± 7 | 97 ± 6 | 88 ± 6 | 87 ± 6 | 79 ± 7* | 70 ± 6* | 44 ± 5* |
| HGM CoA REDUCTASE[d] | 100 ± 7 | 48 ± 6* | 47 ± 6* | 40 ± 4* | 95 ± 6 | 85 ± 7 | 69 ± 6* |
| CHOLESTEROL 7-alpha-HYDROXYLASE[e] | 100 ± 7 | 112 ± 6 | 115 ± 6 | 123 ± 7* | 109 ± 7 | 119 ± 6 | 125 ± 7* |
| ACYL CoA CHOLESTEROL TRANSFERASE[f] | 100 ± 6 | 104 ± 5 | 95 ± 6 | 94 ± 5 | 118 ± 6 | 115 ± 6 | 96 ± 7 |
| NEUTRAL CHOLESTEROL ESTER HYDROLASE[g] | 100 ± 5 | 139 ± 6* | 163 ± 6* | 239 ± 8* | 113 ± 6 | 114 ± 5 | 182 ± 6* |
| ACETYL CoA CARBOXYLASE[h] | 100 ± 5 | 96 ± 7 | 90 ± 7 | 51 ± 6* | 49 ± 6* | 48 ± 5* | 20 ± 5* |
| sn-GLYCEROL-3-PHOSPHATE ACYL TRANSFERASE[i] | 100 ± 6 | 98 ± 7 | 117 ± 8 | 120 ± 7 | 113 ± 7 | 117 ± 7 | 120 ± 6 |
| PHOSPHATIDYLATE PHOSPHOHYDROLASE[j] | 100 ± 7 | 76 ± 7* | 68 ± 6* | 66 ± 5* | 111 ± 6 | 109 ± 5 | 101 ± 6 |

[a]30.8% exchange,
[b]9.2 mg citrate hydrolyzed/g wet tissue/20 min,
[c]10.0 mg acetyl CoA formed/g wet tissue/20 min,
[d]103020 dpm cholesterol formed/g wet tissue/20 min,
[e]289,450 dpm/μg microsomal protein/60 min,
[f]86640 dpm/mg microsomal protein/20 min,
[g]56.436 dpm/mg protein,
[h]43000 dpm/g wet tissue,
[i]87620 dpm/g wet tissue,
[j]μg Pi released/g wet tissue/30 min.

The data from the foregoing Tables 4 and 5 show that the phosphorous-boron adducts of the present invention are potent agents in reducing serum cholesterol and triglycerides in rats and mice orally and I.P., respectively, at 20 mg/kg/day. In mice, compound 3, triethylphosphite-carboxyborane, caused a 41% reduction of serum cholesterol and a 50% reduction of serum triglycerides after 16 days. Compound 4, triethylphosphite-carbomethoxyborane, lowered mouse serum cholesterol 46% and serum triglycerides 54% after 16 days of drug administration at 20 mg/kg/day. Compound 8, the monosodium salt of diethylphosphite-carboxyborane, also proved to be very effective in lowering serum cholesterol levels, by 49%, and serum triglycerides, by 47%, after 16 days in mice.

Compounds 4 and 8 afforded the best hypocholesterolemic activity in mice. Compounds 4 and 6a afforded the best hypotriglycemic activity in mice, with greater than 50% reduction.

Of the compounds tested in rats, compound 8 resulted in the best activity, lowering serum cholesterol levels 48% after 14 days at 20 mg/kg/day, and serum triglycerides by 53%. Compounds 3 and 4 were less active in rats compared to mice; however, they were significantly more potent in rats than clofibrate and lovastatin. Compounds 3, 4, and 8 did not reduce the food consumption of the rats; thus, inhibition of appetite was not a mechanism for lowering blood lipids. Serum lipids over a two-week period were not removed from the blood compartment and placed in tissues of the body. In fact, drug treatment resulted in lowering aortic wall cholesterol levels and triglycerides and phospholipids in the liver and small intestine mucosa. Fecal cholesterol and phospholipids were elevated after drug treatment.

The bile lipids also reflected an increase in the cholesterol content for all three compounds after 14 days administration. The bile flow was increased 15% by compound 3, 13% by compound 4, and was decreased 18% by compound 8. The cholic acid content of the bile was elevated 67%, 7%, and 5% respectively, for compounds 3, 4, and 8, after two-weeks drug administration.

Serum lipoproteins of the rats on day 14 of the treatment demonstrated that cholesterol content was elevated in the chylomicron fraction and the HDL fraction by all three compounds, but was reduced in the VLDL by 8 and in the LDL fraction by compounds 3 and 4. Triglycerides of the LDL fraction were reduced by compounds 4 and 8, and of the VLDL fraction by compounds 3 and 4. Phospholipids were increased in the LDL fraction by compounds 4 and 8, and the HDL fraction by compounds 3 and 4. Protein content of the VLDL fraction was elevated by all three compounds.

In the $CF_1$ mouse liver, compounds 3 and 4 suppressed the activities of ATP-dependent citrate lyase and acetyl CoA synthetase in a concentration dependent manner (Table 6). HMG-CoA reductase activity was suppressed more effectively by compound 3 than 4.

Cholesterol-7α hydroxylase and the neutral cholesterol ester hydrolase activities were significantly elevated by both compounds. Acetyl CoA carboxylase activity was reduced significantly by both 3 and 4 and phosphatidylate phosphohydrolase activity was reduced by compound 3 but not compound 4. Acyl CoA cholesterol acyl transferase and sn - glycerol-3-phosphate acyl transferase activities were not suppressed by either drug at these concentrations.

In summary, the phosphorous-boron derivatives of the present invention have been shown to be potent hypolipidemic agents in rodents, significantly lowering both serum cholesterol and serum triglycerides in rats and mice, and exhibiting effectiveness at the low dose of 20 mg/kg/day, which is not true for many commercially available hypolipidemic agents. In this test system, the phosphorous-boron compounds tested were more potent than clofibrate or lovastatin.

The lipid lowering effects of such phosphorous-boron derivatives appears to be afforded by more than one mechanism. Lipids were being removed from the rat serum compartment and excreted by the bile into the feces, thereby lowering the total body content of lipids. Furthermore, the tested compounds elevated the enzyme activity of cholesterol-7-α-hydroxylase, which is the rate-limiting enzyme for the conversion of cholesterol to cholic acid. The elevation of this latter enzyme activity by the compounds may explain the observation that cholic acid content was elevated in rat bile after 14 days administration of the compounds.

These compounds, in addition, reduced the activities of hepatic de novo enzymes involved in the early cytoplasmic synthesis of fatty acids and cholesterol, i.e., ATP-dependent citrate lyase and acetyl CoA synthetase. The rate-limiting enzyme for cholesterol synthesis, HMG-CoA reductase was also significantly inhibited by the phosphorous-boron derivatives. Acyl CoA cholesterol acyl transferase was not inhibited and neutral cholesterol ester hydrolase activity was accelerated by the compounds. The net effect of drug treatment using the compounds was the removal of cholesterol esters from hepatic storage. The fatty acid synthesis pathway was blocked by the agents at the regulatory site acetyl CoA carboxylase. Phosphatidylate phosphohydrolase, a regulatory enzyme for triglyceride synthesis, was also inhibited by compound 3. sn-glycerol-3-phosphate acyl transferase, the other regulatory site in the triglyceride pathway, was not inhibited by the phosphorous-boron compounds. Reduction in tissue lipid levels, e.g., liver, aorta, and small intestine, are observed after in vivo administration of these drugs, suggesting that their enzyme sites are viable targets of these drugs.

After 14 days administration of the phosphorous-boron compounds to rats, the serum lipoprotein lipid content was modulated in a manner which suggests that the compounds may be useful clinically to treat cardiovascular-related atherosclerosis. As this disease develops in humans, the LDL-cholesterol content is elevated and the HDL-cholesterol content is reduced. This has been shown to be a risk factor in precipitating myocardial infarctions in humans. Studies have demonstrated that by elevating the HDL-cholesterol and lowering the LDL-cholesterol in humans, the incidence of infarctions was reduced after drug treatment. The use of boron-containing derivatives of the present invention achieved a favorable ratio with regard to LDL and HDL cholesterol levels in rats. The LDL cholesterol is responsible for the deposition of cholesterol in plaques on the arterial walls. The HDL is responsible for the transport of cholesterol from the plaques to the liver for excretion from the body. The phosphonoacetate boron analogs of the present invention achieve higher HDL-cholesterol content after 14 days treatment, suggesting that these compounds may be of clinical use in the future.

EXAMPLE XXIX

Anti-inflammatory Activity of Phosphorous-Boron Adducts $CF_1$ male mice (~25g) were administered test drugs at 8 mg/kg in 0.0% Tween ® 80-$H_2O$ intraperitoneally 3hr. and again 30 min. prior to the injection of 0.2 ml of 1% carrageenan in 0.9% saline into the planar surface of the right hind foot. Saline was injected into the left hind foot which serves as a base line. After 3 hours, both feet were excised at the tibiotarsal (ankle)s joint according to the modified method of Winter (Winter et. al., *Proc. Soc. Exp. Biol. Med.* 1962, 111, 544–547, and Hendershot and Forsaith, *J. Pharmacol. Exp. Ther.* 1970, 175, 435–442). The control mice afforded a 78±3 mg increase in the paw weight. Data are presented in Table 7 below.

TABLE 7
THE ANTI-INFLAMMATORY ACTIVITY OF BORON ANALOGUES OF PHOSPHONOACETATES IN $CF_1$ MICE AT 8 MG/KG

| Compound | Percent of Control |
|---|---|
| 1 | 94.4 |
| 2 | 64.3 |
| 5a | toxic |
| 5b | 55.8 |
| 5c | 66.5 |
| 6a | 89.3 |
| 7a | 70.3 |
| 13 | 73.9 |

While the invention has been described herein with reference to illustrative compounds and specific embodiments of the invention, it will be appreciated that numerous variations, modifications, and other embodiments are possible, and accordingly, all such variations, modifications, and embodiments are to be regarded as being within the spirit and scope of the invention.

What is claimed is:

1. A phosphite-borane compound corresponding to the general formula:

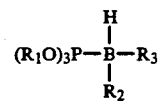

wherein:
each $R_1$ is independently selected from: H; $C_1$-$C_{10}$ alkyl; alkylaryl; aralkyl; aryl; monovalent metal ions; and quaternary ammonium cations of the formula $(R_4)_4N^+$, wherein each $R_4$ is independently selected from H and $C_1$-$C_{10}$ alkyl;
$R_2$ is selected from H and $C_1$-$C_{10}$ alkyl; and
$R_3$ is selected from $CNCH_2CH_3^+BF_4^-$, COOH, carboxyl salts, $COOR_5$, and $CONHR_5$, wherein $R_5$ is selected from $C_1$-$C_{10}$ alkyl, alkylaryl, aralkyl, and aryl, with the proviso that if at least one of the $R_1$ substituents is H, monovalent metal ion, or quaternary ammonium cation, then $R_3$ may also be CN.

2. A phosphite-borane compound according to claim 1, wherein $R_2$ is H.

3. A phosphite-borane compound according to claim 1, wherein:
$R_1$ is independently selected from: H, $C_1$-$C_{10}$ alkyl, and monovalent ions Na and $(n-C_4H_9)_4N^+$;
$R_2$ is H; and
$R_3$ is selected from $CNCH_2CH_3^+BF_4^-$, COOH, $COOCH_3$ and $CONHC_2H_5$.

4. A phosphite-borane compound according to claim 1, wherein:
$R_1$ is $CH_2CH_3$;
$R_2$ is H; and
$R_3$ is selected from $CNCH_2CH_3^+BF_4^-$, COOH, $COOCH_3$ and $CONHC_2H_5$.

5. A phosphite-borane compound according to claim 1, wherein:
one of the $R_1$ substituents is selected from H, Na, and $(n-C_4H_9)_4N^+$;
the other two $R_1$ substituents are $CH_2CH_3$;
$R_2$ is H; and
$R_3$ is selected from CN, $CNCH_2CH_3^+BF_4^-$, COOH, $COOCH_3$ and $CONHC_2H_5$.

6. A phosphite-borane compound according to claim 1, wherein:
one of the $R_1$ substituents is $CH_2CH_3$;
the other two $R_1$ substituents are selected from H, $Na^+$ and $(n-C_4H_9)_4N^+$;
$R_2$ is H; and
$R_3$ is CN.

7. A phosphite-borane compound according to claim 1, wherein: $R_1$ is $Na^+$;
$R_2$ is H; and
$R_3$ is CN.

8. A phosphite-borane compound according to claim 4, wherein $R_3$ is selected from COOH, $COOCH_3$ and $CONHC_2H_5$.

9. A phosphite-borane compound according to claim 5, wherein $R_3$ is selected from CN, COOH, $COOCH_3$ and $CONHC_2H_5$.

10. A phosphite-borane compound according to claim 5, wherein $R_3$ is selected from COOH, $COOCH_3$ and $CONHC_2H_5$.

11. A pharmaceutical formulation comprising a therapeutically effective amount of a phosphite-borane compound in a pharmaceutically acceptable carrier, the said phosphite-borane compound comprising a boron-containing moiety bonded to the phosphorus atom of the phosphite moiety of the compound, wherein the boron-containing moiety is selected from: $BH_2CN$; $BH_2CNC_2H_5^+BF_4^-$; $BH_2COOR$; and $BH_2CONHR$ and wherein the phosphorous atom is covalently bonded to OR substituents; wherein each R is selected from: H, $C_1$-$C_{10}$ alkyl; alkylaryl; aralkyl; aryl; monovalent metal ions; and quaternary ammonium cations of the formula $(R_4)_4N^+$, wherein each $R_4$ is independently selected from H and $C_1$-$C_{10}$ alkyl.

12. A pharmaceutical formulation according to claim 11, wherein the phosphite moiety is $(R_1O)_3P$ wherein each $R_1$ is independently selected from: H; $C_1$-$C_{10}$ alkyl; alkylaryl; aralkyl; aryl; nucleosides; monovalent metal ions; and quaternary ammonium ions of the formula $(R_4)_4N^+$, wherein each $R_4$ is independently H or $C_1$-$C_{10}$ alkyl.

* * * * *